United States Patent
Barranco

(10) Patent No.: US 7,671,044 B2
(45) Date of Patent: Mar. 2, 2010

(54) PHARMACEUTICAL FORMULA FOR TREATING SKIN DISEASE

(75) Inventor: Enrique Rossell Barranco, Madrid (ES)

(73) Assignee: Klever Mode, S.L., Madrid (ES)

( * ) Notice: Subject to any disclaimer, the term of this patent is extended or adjusted under 35 U.S.C. 154(b) by 687 days.

(21) Appl. No.: 11/521,073

(22) Filed: Sep. 14, 2006

(65) Prior Publication Data

US 2008/0045487 A1 Feb. 21, 2008

(30) Foreign Application Priority Data

Aug. 17, 2006 (EP) .................... 06380229

(51) Int. Cl.
- *A01N 45/00* (2006.01)
- *A61K 31/56* (2006.01)
- *A61K 31/505* (2006.01)
- *C07J 1/00* (2006.01)

(52) U.S. Cl. ............. 514/171; 514/177; 514/178; 514/269; 552/622

(58) Field of Classification Search ............ 514/171, 514/177, 178, 269, 272; 552/622
See application file for complete search history.

(56) References Cited

U.S. PATENT DOCUMENTS

2004/0225140 A1 * 11/2004 Fernandez et al. .......... 552/500

FOREIGN PATENT DOCUMENTS

WO     WO 9949895    * 10/1999

* cited by examiner

*Primary Examiner*—Sreeni Padmanabhan
*Assistant Examiner*—Sarah Pihonak
(74) *Attorney, Agent, or Firm*—Klauber & Jackson, LLC

(57) ABSTRACT

The present invention refers to a pharmaceutical formulation characterized in that it includes mainly clobetasolpropionate, minoxidil and 11 alpha hydroxyprogesterone as main active principles, besides other excipients, vitamins and/or minerals, and to its use in the treatment of skin diseases, mainly in the symptomatic treatment of psoriasis.

8 Claims, No Drawings

PHARMACEUTICAL FORMULA FOR TREATING SKIN DISEASE

CROSS REFERENCE TO RELATED APPLICATIONS

The present application claims priority from European Patent Application Serial No. 06380229.2 filed on Aug. 17, 2006. Applicant claims priority under 35 U.S.C. §119 as to the said European application, and the entire disclosure of that application is incorporated hererein by reference.

FIELD OF THE INVENTION

The present invention belongs to the area of development of a topical use pharmaceutical formula intended to treat skin diseases, mainly to be used in the symptomatic treatment of psoriasis.

STATE OF THE ART PRIOR TO THE INVENTION

Psoriasis is a chronic skin disease characterized by the appearance of erythrematic squamous plaques that, although it can affect any skin site, affects preferentially the scalp, elbows, knees, lumbosacral region, nails, etc . . . This disease affects approximately between 0.05 and 4.8% of the world's population. This is a condition of multi-factorial origin, but with a genetic base and a significant immunological participation of the digestive system, although its cause is unknown.

The main and most evident alteration caused by psoriasis is the epidermal cellular hyperproliferation. Under normal conditions, cells located in the basal stratum of the epidermis divide by mitosis, originating two new cells that continue to mature and ascend to upper strata until they reach the corneal stratum where their keratinization process is completed. After approximately twenty-eight days from their birth in the basal stratum they die and become detached from the skin, breaking off. Psoriasis skin is characterized in that the growth cycle described above is completed, instead, in only 4 days. In this manner the keratinocytes accumulate and the skin becomes hyperplastic. Clinically, this condition is manifested by thick plaques with abundant scales. The factors that promote this epidermal response are continuously being researched. Although there is a complex interrelation between the epidermal and the dermal cells with the release of multiple cytokines, neuropeptides and other substances that participate in the inflammation process, it seems that the most important cell, and perhaps the trigger factor that activates hyperproliferation of keratinocytes, is the T lymphocyte.

Some haplotypes of the main histocompatibility system (HLA) have been related to psoriasis, mainly HLA-Cw6. The discovery of a susceptibility gene for family psoriasis was recently reported. This gene is located in the distal end of the long arm of chromosome 17. Large groups of twins have been studied, in which at least one of the two twins suffered from psoriasis, finding that in dizygotic pairs the concordance of the disease is of 23%, while in monozygotic twins it is of 70%. Since concordance in monozygotic twins is not 100%, as should occur in the case of a genetic disease, it is obvious that there is an important contribution of environmental factors. The importance of *Streptococcus pyogenes* participation has been demonstrated in the case of droplet psoriasis.

There are affected people that express what has been called the Köebner phenomenon, consisting in developing a psoriasis plaque after having suffered a skin trauma (such as a scratch or abrasion) over the damaged area and exhibiting the same morphology.

Multiple pharmaceutical drugs have been associated to the exacerbation of psoriasis, most notably Lithium, but also anti-paludism beta-blockers or corticosteroidal suppression. Nicotine addiction, alcoholism and stress among other factors, may also modify the severity of the disease, although this has not been fully demonstrated.

Treatment of psoriasis may be considered an art. There are few conditions for which so many therapeutic options have been described. This plurality of pharmaceutical drugs and/or therapeutic options can be somehow considered beneficial, since it allows individualizing each treatment knowing there are other agents that may be used in case of lack of efficacy or side effects. On the other hand, it is also indicative of the lack of existence of an infallible, or at least useful, agent or therapeutic method for the majority of affected people.

When the affected suffer only a few lesions or mild psoriasis, the advisable treatment must be based on topical agents. The best known agents are coal tar, antralin, topical corticosteroids, calcipotriol, keratinocytes, phototherapy with ultraviolet B radiation, photochemiometry (psoralen), systemic corticosteroids, methotrexate, cyclosporine and etrethinate or acithretin, both synthetic retinoids.

DESCRIPTION OF THE INVENTION

The present invention refers to a pharmaceutical formulation and its use in the treatment of skin diseases, preferably symptomatic treatment of psoriasis.

Psoriasis is a condition that affects both genders equally. Psoriasis incidence is lower in those younger than 40 years old, although the risk of arthropatic psoriasis and psoriasis in various members of the same family is greater in thisage group (type I psoriasis), compared to those in which the onset occurs after 40 years of age.

The characteristic psoriasis lesion is the erythrematic squamous plaque. The scale is white and strongly adhered to the plaque; if bleeds if removed from the underlying skin. On rare occasions, it is so abundant that it may resemble the appearance of oyster shells or tree bark (ostraceous or rupiaceous psoriasis respectively). Depending on the topography, some lesions may be erythremic and without scales (such as in skin folds, face and mucous membranes). The plaques may be of varying sizes and shapes, but usually they serve to easily identify the disease. Most affected people do not report symptoms, but some suffer pruritus on the lesions.

Although the condition appears preferentially on the scalp, elbows, knees, anterior side of the legs, lumbosacral region, palms of the hands, sole of the feet and the nails, it may affect any other skin site. Participation of oral or genital mucosa participation occurs in approximately 10% of cases. In the mouth, lesions are usually indistinguishable from the geography of the tongue. In the genitals, those affected may present erythrematic squamous plaques or erythrematic spots without scales, and even exulcerations.

A group of affected people, generally adolescents or young adults, may experience an acute onset of the disease, with the sudden appearance of multiple small lesions (smaller than 1 cm) spread throughout the entire body. This clinical manifestation is called droplet psoriasis and it is frequently associated to a recent streptococcal infection.

Some patients may present very severe and symptomatic manifestations of psoriasis, accompanied by fevers, acute general attack frequently with associated arthropathy. One of these clinical manifestations is psoriatic erythrodermia, in which 100% of the body's surface is affected by lesions that are generally are more erythrematous than scaly. Another severe manifestation is pustulent psoriasis in which, besides some psoriasic plaques or erythrodermia, there are pustulent lesions.

Up to 15% of patients are affected in one or more joints (arthropathic psoriasis). The most frequent clinical forms are: asymmetric oligoarthrosis (70% of cases), distal interphalangeal, mutilating arthritis, symmetric polyarthritis and the spinal (axial) form.

Generally, these clinical manifestations appear once the psoriasis has been firmly diagnosed, although arthropathies may precede dermatosis.

In general, there is a correlation between the severity of psoriasis and the development of psoriatic arthritis. In 97% of cases this rheumatoid factor is negative.

Nails are frequently affected, the most common alterations being the presence of puntiform depressions of the ungueal plate (pitting), onycholysis, subungueal hyperkeratosis, erythrema of the ungueal bed and clear dystrophia.

The present invention refers to a pharmaceutical formulation wherein it contains, at least, the following active principles:

Clobetasolpropionate
Minoxidil, and
11 alpha hydroxyprogesterone.

According to the preferred embodiment, said active principles are present in the following percentage intervals in relation to the total weight of the formulation:

Clobetasolpropionate: 0.05-5%
Minoxidil: 0.05-7%, and
11 alpha hydroxyprogesterone: 0.05-12%

The preferred interval distribution is as follows:
Clobetasolpropionate: 0.1-2%
Minoxidil: 0.1-5%, and
11 alpha hydroxyprogesterone: 0.1-10%.

According to a particular embodiment, the pharmaceutical formulation object of the present invention may also include, besides the active principles, one excipient at the least. This excipient is selected, preferably, from hydroalcoholic solutions, O/W emulsions, W/O emulsions, vaselines, lanolines, oleo-calcareous solutions, cellulose solutions and combinations thereof. According to that described above, O/W emulsions are understood to be emulsions of oil in water, while the W/O emulsions are emulsions of water in oil. In this manner the formulation of the present invention may be manufactured with different types of excipients, selected from those listed above.

According to another particular embodiment, the pharmaceutical formulation may also contain, at least, one vitamin and/or mineral.

Preferably, the vitamins are selected from vitamin D, vitamin E, vitamin F, vitamin H, vitamin A, B complex and combinations thereof. Also, in a preferred manner, the minerals are selected from calcium, copper, iodine, magnesium and combinations thereof.

According to the particular preferred embodiment of the present invention, the pharmaceutical formulation comprises clobetasolpropionate, minoxidil, 11 alpha hydroxyprogesterone, propylenglycol, distilled water and alcohol. According to this particular embodiment, the pharmaceutical formulation comprises, preferably, 0.15 g of clobetasolpropionate, 1 g of minoxidil, 0.75 g of 11 alpha hydroxyprogesterone, 10 ml of propylenglycol, 20 ml of distilled water and 70 ml of alcohol.

The modus operandi of the formulation in the various presentations is described in the pharmaceutical and pharmacopean description forms that describe how to prepare the excipients to add the necessary active principles, vitamins and minerals.

The pharmaceutical formulation of the present invention may be presented in different galenic forms. Preferably, the galenic form will be selected from lotion, emulsion, cream, gel, shampoo, liniment, powder, solutions and combinations thereof.

Also, the present invention refers in addition, to the use of the pharmaceutical formulation in the treatment of skin diseases, preferably, in the symptomatic treatment of psoriasis.

The pharmacological action of the active principles of the present invention is mainly that of a peripheral vasodilator, the main action of minoxidil, corticoidal anti-inflammatory action due to clobetasolpropionate and the hormonal action on the affected area produced by the 11 alpha hydroxylprogesterone.

Progesterone is a steroidal hormone, a compound with the same chemical core as female estrogenic hormones and male androgenic hormones, as well as that of cholesterol and suprarenal steroidal hormones. The substances that imitate the action of progesterone are sometimes called progestagenic agents and are used with synthetic estrogens as oral contraceptives and as hormonal substitution therapy in post-menopausal women.

The 11 alpha hydroxylprogesterone hydrochloride (DCI), according to its pharmacology, is used, besides as a progestagenic as indicated in the previous paragraph, for its anti-androgenic properties in the reduction of sebaceous production in patients suffering from seborrhea and alopecia. This property of 11 alpha hydroxylprogesterone is applied to patients with psoriasis since it reduces the fat in the affected area while allowing the remaining active principles to act on the condition. Seborrhea is a condition of the skin's sebaceous glands characterized by the increase and alteration of the sebaceous secretion (fatty material produced by these glands).

The mechanism by which the formulation of the present invention exerts its action is based, amongst others, in its vasodilator effect (increase of blood flow) thus eliminating the toxins produced by psoriatic pathologies that have a digestive background of degenerative origin.

There are some contraindications to be considered, such as hypersensitivity to any of the present invention formulation's components. It is also not indicated during pregnancy or breastfeeding and for children younger than 16 years of age. In these patients it is advisable to do periodical clinical check ups.

Asymptomatic treatment of psoriasis with the pharmaceutical formulation of the present invention must not last more than 15 consecutive days, although it is possible to resume treatment after a 7 day rest. The pharmaceutical formulation in any of its possible galenic forms must be applied on the affected area once a day (avoiding contact with eroded areas in the skin, lesions, mucous membranes and eyes). If the patient has many affected areas, it is advisable to apply the formulation in one or two areas at a time, and when these areas improve, apply in different areas (two-area application at a time is always recommended). Application in all areas at the same time is not recommended.

Once the symptoms have improved after application of the pharmaceutical formulation of the present invention, it is advisable to rest until the symptoms appear again.

It can be concluded, based on the clinical trials, that the efficacy of the pharmaceutical formulation of the present invention is noteworthy, especially as shown in Example 2, for the treatment of psoriasis. Its innocuousness and fastacting properties are remarkable, the first results having appeared during the first two days of use. These clinical trials show that the pharmaceutical formulation delays the accelerated growth of the skin cells, as well as its capacity to eliminate the rest of anomalies concurrent in cases of common psoriasis. Also noteworthy is that treatment with the pharmaceutical formulation of the present invention has not provoked changes in skin color in any of the patients, therefore being appropriate for facial use or in any other visible area of the body. Also, other side effects that have appeared are of little relevance, as shown in Example 2. The convenience of use of the formulation and the small quantity necessary to cause improvement in a large affected area make the treatment with the pharmaceutical formulation of the present invention very advantageous.

EXAMPLES

The following example of embodiment of the present invention is intended as a descriptive, but not limiting example, of the scope of said invention.

Example 1

Preparation of the Pharmaceutical Formulation for Treatment of Skin Diseases

First, 20 ml of distilled water are introduced in a vessel. 0.15 g of clobetasolpropionate and 0.75 g of 11 alpha hydroxyprogesterone are weighed and added to the vessel containing the distilled water and a stirrer is introduced until complete dispersion is achieved.

The second step entails introducing 70 ml of alcohol in a vessel and weighing 1 g of minoxidil that is added to the vessel containing the alcohol solute, then a magnetic stirrer is introduced until complete dispersion is achieved. The next step is to add 10 ml of propylenglycol.

The last step is to transfer the contents of the first precipitation vessel (first step) into the second, keeping the stirring, until transparency is achieved.

Example 2

Application of the Pharmaceutical Formulation Obtained in Example 1 in Patients with Psoriasis The formulation prepared in Example 1 has been used in patients with psoriasis. The screening criteria for said patients, who have submitted to the treatment voluntarily, are:
patients affected by common psoriasis
ages between 18 and 65 years of age (men and women)
More than 20% of the body's surface affected by the condition
Not having received any type of general treatment during at least one month prior to treatment with the pharmaceutical formulation of the present invention
Not having received any type of treatment (including preventative treatments) in the affected areas at least during a week before treatment with the pharmaceutical formulation of the present invention.

According to these screening criteria, the efficacy of the formulation described in Example 1 is apparent, in an obvious manner, a few days after initiating the treatment, between 2 and 4 days. The efficacy rate obtained is of 97%. Only 4.2% of treated patients suffered some side effects, all of them being irrelevant.

The invention claimed is:

1. Pharmaceutical formulation wherein it includes 0.15 g of clobetasol propionate, 1 g of minoxidil, 0.75 g of 11 alpha hydroxyprogesterone, 10 ml of propylene glycol, 20 ml of distilled water, and 70 ml of alcohol.

2. Pharmaceutical formulation according to claim 1 wherein, in addition, it contains at least one excipient.

3. Pharmaceutical formulation according to claim 2, wherein excipient is selected from hydroalcoholic solutions, O/W emulsions, W/O emulsions, vaselines, lanolines, oleocalcareous solutions, cellulose solutions and combinations thereof.

4. Pharmaceutical formulation according to claim 1 wherein, in addition, it contains at least one vitamin and/or mineral.

5. Pharmaceutical formulation according to claim 4 wherein vitamins are selected from vitamin D, vitamin E, vitamin F, vitamin H, vitamin A, B complex and combinations thereof.

6. Pharmaceutical formulation according to claim 4 wherein said minerals are selected from calcium, copper, iodine, magnesium and combinations thereof.

7. Pharmaceutical formulation according to claim 1 wherein it may be presented in a galenic form selected from lotion, emulsion, cream, gel, shampoo, liniment, powder, solutions and combinations thereof.

8. A method for the treatment of psoriasis wherein said method comprises the application of a pharmaceutical formulation comprising 0.15 g. of clobetasol propionate, 1 g of minoxidil, 0.75 g of 11 alpha hydroxyprogesterone, 10 ml of propylene glycol, 20 ml of distilled water and 70 ml of alcohol.

* * * * *